US008150628B2

(12) United States Patent
Hyde et al.

(10) Patent No.: US 8,150,628 B2
(45) Date of Patent: Apr. 3, 2012

(54) ESTABLISHING A BIOLOGICAL RECORDING TIMELINE BY ARTIFICIAL MARKING

(75) Inventors: Roderick A. Hyde, Livermore, CA (US); Edward K. Y. Jung, Bellevue, WA (US); Royce A. Levien, Lexington, MA (US); Robert W. Lord, Seattle, WA (US); Mark A. Malamud, Seattle, WA (US); John D. Rinaldo, Jr., Bellevue, WA (US); Lowell L. Wood, Jr., Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1056 days.

(21) Appl. No.: 11/343,944

(22) Filed: Jan. 31, 2006

(65) Prior Publication Data
US 2007/0156346 A1  Jul. 5, 2007

Related U.S. Application Data

(63) Continuation-in-part of application No. 11/323,832, filed on Dec. 30, 2005.

(51) Int. Cl.
*G01N 33/48* (2006.01)
*C12Q 1/00* (2006.01)
(52) U.S. Cl. .............................. 702/19; 435/4
(58) Field of Classification Search .................. None
See application file for complete search history.

(56) References Cited

U.S. PATENT DOCUMENTS

| | | | |
|---|---|---|---|
| 5,472,403 | A | 12/1995 | Cornacchia et al. |
| 5,616,471 | A | 4/1997 | Yuspa |
| 6,306,087 | B1 | 10/2001 | Barnhill et al. |
| 6,808,875 | B2 | 10/2004 | Hellerstein |
| 7,108,690 | B1 | 9/2006 | Lefki et al. |
| 7,594,889 | B2 | 9/2009 | St. Ores et al. |
| 2003/0023235 | A1 | 1/2003 | Cense et al. |
| 2003/0153820 | A1 | 8/2003 | Berner et al. |
| 2004/0122708 | A1* | 6/2004 | Avinash et al. .................. 705/2 |
| 2004/0166532 | A1 | 8/2004 | Keller |
| 2005/0096511 | A1 | 5/2005 | Fox et al. |
| 2005/0209514 | A1 | 9/2005 | Oshima et al. |

FOREIGN PATENT DOCUMENTS

| | | |
|---|---|---|
| EP | 1068861 A | 1/2001 |
| WO | WO 00/11469 A | 3/2000 |
| WO | WO 00/62700 A1 | 10/2000 |

OTHER PUBLICATIONS

Sato et al., "Induction of the hair growth phase in postnatal mice by localized transient expression of Sonic hedgehog," The Journal of Clinical Investigation, vol. 104 (1999) pp. 855-864.*
Kalasinsky, "Drug Distribution in Human Hair by Infrared Microscopy," Cellular and Molecular Biology, vol. 44, pp. 81-87.*
Mandl et al. "Understanding Immune Cell Trafficking Patterns Via in Vivo Bioluminescence Imaging," Journal of Cellular Biochemistry Supplement, vol. 39, pp. 239-246 (2002).*
Kempson et al. "ToF-SIMS analysis of elemental distributions in human hair," (Science of the Total Environment, vol. 338 (2005) pp. 213-227).*
"Abstracts—2004 US Symposium of the International Society for Bioengineering and the Skin (ISBS), Orlando Florida, USA"; Skin Research and Technology; bearing dates of Oct. 28-30, and 2004; pp. 1-16; vol. 10; Blackwell Munksgaard.
Bakhtiar, R.; Tse, F.L.S.; "Biological mass spectrometry: a primer"; Mutagenesis; bearing dates of: received on Jan. 5, 2000 and 2000; accepted on May 9, 2000; pp. 415-430; vol. 15; No. 05; UK Environmental Mutagen Society/Oxford University Press.
Cerling, Thure E. et al, "Stable isotopes in Elephant Hair Document Migration Patterns and Diet Changes"; Proceedings of the National Academy of Sciences; bearing dates of Jan. 10, 2006 and contributed by Cerling on Nov. 4, 2005; vol. 103, Issue 2; pp. 371-373; located at www.pnas.org/cgi/doi/10.1073/pnas.0509606102.
"Drug Screening: Patented Technology"; bearing a date of 2004; pp. 1-2; Psychemedics Corporation; located at: http://psychemedics.com/frequent.htm; printed on Dec. 7, 2005.
"Hair Drug Screening Test—PDT-90® Personal Forensic Drug of Abuse Testing Service"; bearing a date of 12-8-105(sic) 2005; Copyright © 1997 © 1999 © 2005; pp. 1-3; Craig Medical Distribution, Inc.; located at: http://www.craigmedical.com/Hair_Drug_Test.htm; printed on Dec. 8, 2005.
"Hair Drug Testing FAQ—PDT-90® Forensic Drug of Abuse Hair Testing"; bearing a date of 12-8-105(sic) 2005; Copyright © 1997 © 1999 © 2005; pp. 1-4; Craig Medical Distribution, Inc.; located at: http://www.craigmedical.com/Hair_Drug_Test_FAQ.htm; printed on Dec. 8, 2005.
"Hair Drug Testing"; bearing dates of last revision made Dec. 1, 2005 and 2000; pp. 1-3; Home Health Testing®; AbDiagnostics, Inc.; located at: http://www.homehealthtesting.com/hair-drug-tests.htm; printed on Dec. 7, 2005.
Harkey, M.R.; "Anatomy and physiology of hair"; Forensic Science International; bearing dates of 1993 and accepted on Dec. 10, 1992; vol. 63; pp. 9-18; Elsevier Scientific Publishers Ireland Ltd.
Henderson, G.L.; "Mechanisms of drug incorporation into hair"; Forensic Science International; bearing dates of 1993 and accepted on Dec. 10, 1992; vol. 63; pp. 19-29; Elsevier Scientific Publishers Ireland Ltd.
"Identa Confirm Substance Tests"; bearing dates of last revisions made Dec. 1, 2005 and 2000; pp. 1-2; Home Health Testing®—AbDiagnostics, Inc.; located at: http://www.homehealthtesting.com/identa-confirm.htm; printed on Dec. 7, 2005.
Keis, Karin and Kamath, Yash K.; "Reference Section: Objective Measurement of Hair Lustre"; bearing a date of 2004; pp. 1-5; Business Briefing: Global Cosmetics Manufacturing.
Koren, Gideon; "Hair testing and maternal drug exposure. (Drugs, Pregnancy, and Lactation)";Family Practice News 35.18; bearing dates of Sep. 15, 2005 and 2005; pp. 45 (1) (pp. 1-3); Thomson Gale—Thomson Corporation and International Medical News Group; King County Library System; printed on Dec. 27, 2005.

(Continued)

*Primary Examiner* — Marjorie Moran
*Assistant Examiner* — Anna Skibinsky (57) ABSTRACT

A method and system are described for transmitting a timing estimate record responsive to a systemic flow of one or more artificial markers.

10 Claims, 7 Drawing Sheets

OTHER PUBLICATIONS

Kreplak, L.; Briki, F.; Duvault, Y.; Doucet, J.; Merigoux, C.; Leroy, F.; Lévêque, J.L.; Miller, L.; Carr, G.L.; Williams, G.P.; and Dumas, P.; "Profiling lipids across Caucasian and Afro-American hair transverse cuts, using synchrotron infrared microspectrometry"; International Journal of Cosmetic Science; bearing dates of: received Mar. 17, 2001; accepted Aug. 4, 2001 and 2001; pp. 369-374; vol. 23; Blackwell Science Ltd.

Ley, Brian; "Diameter of a Human Hair—The Physics Factbook"; bearing a date of 1999; pp. 1-1; located at: http://hypertextbook.com/facts/1999/BrianLey.shtml; printed on Dec. 27, 2005.

Marschner, Stephen R.; Jensen, Henrik Wann; Cammarano, Mike; Worley, Steve; Hanrahan, Pat; "Light Scattering from Human Hair Fibers"; pp. 1-12.

Masukawa, Yoshinori; Tsujimura, Hisashi; Imokawa, Genji; "A systematic method for the sensitive and specific determination of hair lipids in combination with chromatography"; Journal of Chromatography B; bearing dates of: received on Feb. 27, 2005; accepted on Jun. 12, 2005; available online date of Jul. 11, 2005 and 2005; pp. 131-142; vol. 823; Elsevier B.V.; located at: www.sciencedirect.com and www.elsevier.com/locate/chromb.

"Mineral & Toxic Element Tests"; Home Health Testing; bearing dates of 2000 and Last Revision date of Dec. 1, 2005; pp. 1-2; Home Health Testing®—AbDiagnostics, Inc.; located at: http://www.homehealthtesting.com/mineral-tests.htm; printed on Dec. 7, 2005.

Reyes, Darwin R.; Lossifidis, Dimitri; Auroux, Pierre-Alain; Manz, Andreas; "Micro Total Analysis Systems. 1. Introduction, Theory, and Technology"; Analytical Chemistry; bearing dates of Jun. 15, 2002, May 17, 2002 and 2002; pp. 2623-2636; vol. 74, No. 12; American Chemical Society.

Sachs, Hans; Kintz, Pascal; "Review: Testing for drugs in hair Critical review of chromatographic procedures since 1992"; Journal of Chromatography B; bearing date of 1998; pp. 147-161; vol. 713; Elsevier Science B.V.

Sobottka, Gerrit; Weber, Andreas; "Übersicht über die optischen Eigenschaften von Human-Haar"; Computer Graphics Technical Reports, CG-2002/1; bearing a date of Apr. 12, 2002; pp. 1-8; Institut für Informatik II, Universität Bonn; Bonn, Germany.

Stamm, Robert F.; Garcia, Mario L.; Fuchs, Judith J.; "The optical properties of human hair I. Fundamental considerations and goniophotometer curves"; Journal of the Society of Cosmetic Chemists; bearing dates of Nov. 17, 1976, Sep. 1977; vol. 28, No. 9; pp. 571-599; The Society of Cosmetic Chemists, Inc.

Thormann, Wolfgang; Lurie, Ira S.; McCord, Bruce; Marti, Ulrich; Cenni, Bruno; Malik, Naseem; Advances of capillary electrophoresis in clinical and forensic analysis (1999-2000); Electrophoresis; bearing dates of Jul. 17, 2001 and 2001; pp. 4216-4243; vol. 22; Wiley-VCH Verlag GmbH, 69451 Weinheim, 2001.

Verpoorte, Elisabeth; "Microfluidic chips for clinical and forensic analysis"; Electrophoresis; bearing dates of Dec. 27, 2001 and 2002; pp. 677-712; vol. 23; Wiley-VCH Verlag GmbH, 69451 Weinheim, 2002.

Ward, Kelly; Galoppo, Nico; Lin, Ming C.; "Modeling Hair Influenced by Water and Styling Products"; pp. 1-8; University of North Carolina at Chapel Hill.

PCT International Search Report; International Application No. PCT/US 06/48972; pp. 1-3; dated Jan. 28, 2008.

U.S. Appl. No. 11/343,966, Hyde et al.

PCT International Search Report; International Application No. PCT/US 06/48605; pp. 1-2; dated Mar. 28, 2008.

Favretto, Donata; Frison, Giampietro; Vogliardi, Susanna; Ferrara, Santo Davide; "Research Article: Potentials of Ion Trap Collisional Spectrometry for Liquid Chromatography/Electrospray Ionization Tandem Mass Spectrometry Determination of Buprenorphine and Nor-Buprenorphine in Urine, Blood and Hair Samples"; Rapid Communications in Mass Spectrometry; bearing a date of Mar. 20, 2006; pp. 1257-1265; vol. 20, No. 8; John Wiley & Sons, Ltd.

Mekota, Anna-Maria; Grupe, Gisela; Ufer, Sandra; Cuntz, Ullrich; "Research Article: Serial Analysis of Stable Nitrogen and Carbon Isotopes in Hair: Monitoring Starvation and Recovery Phases of Patients Suffering from Anorexia Nervosa"; Rapid Communications in Mass Spectrometry; bearing a date of Apr. 20, 2006; pp. 1604-1610; vol. 20, No. 10; John Wiley & Sons, Ltd.

Adonai, Nora; "Ex Vivo Cell Labeling with $^{64}$Cu-Pyruvaldehyde-bis ($N^4$-methylthiosemicarbazone) for Imaging Cell Trafficking in Mice with Positron-Emission Tomography"; PNAS: Medical Sciences; dated Feb. 26, 2002; located at: http://www.pnas.org/cgi/content/abstract/052709599v1 [Abstract Attached].

PCT International Search Report; International Application No. PCT/US 07/01718; pp. 1-2; dated Oct. 3, 2007.

Bantignies et al.; "Chemical imaging of hair by infrared microspectroscopy using synchrotron radiation"; bearing a date of Mar./Apr. 2000; pp. 73-90; vol. 51; Journal of Cosmetic Science.

Janda et al.; "Determination of ethyl glucuronide in human hair by SPE and LC-MS/MS"; bearing a date of 2002; pp. 59-65; vol. 128; Forensic Science International; Elsevier Science Ireland Ltd.

Supplementary Partial European Search Report; European App. No. EP 06 85 1952; Nov. 27, 2009 pp. 1-6.

Nakano, M., et al.; "Using Ofloxacin As a Time Marker in Hair Analysis For Monitoring the Dosage History of Haloperidol"; Eur J Clin Pharmacol; 1994; pp. 195-202; vol. 47; Springer-Verlag.

European Patent Office Search Report; App. No. EP 06 851 952.9; Nov. 8, 2011; pp. 1-4.

Saito et al.; "Determination of chronic methamphetamine abuse by hair analysis"; Forensic Science International; 2000; pp. 65-71; vol. 112; Elsevier Science Ireland Ltd.

* cited by examiner

ESTABLISHING A BIOLOGICAL RECORDING TIMELINE BY ARTIFICIAL MARKING

RELATED APPLICATIONS

For purposes of the USPTO extra-statutory requirements, the present application constitutes a continuation-in-part of U.S. patent application Ser. No. 11/323,832, entitled MODULATING A BIOLOGICAL RECORDING WITH ANOTHER BIOLOGICAL RECORDING, naming Roderick A. Hyde; Edward K. Y. Jung; Royce A. Levien; Robert W. Lord; Mark A. Malamud; John D. Rinaldo, Jr. and Lowell L. Wood, Jr. as inventors, filed 30 Dec. 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/343,966, entitled USING A BIOLOGICAL RECORDING TO OBTAIN TIME VALUES, naming Roderick A. Hyde; Edward K. Y. Jung; Royce A. Levien; Robert W. Lord; Mark A. Malamud; John D. Rinaldo, Jr. and Lowell L. Wood, Jr. as inventors, filed contemporaneously herewith, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

All subject matter of the Related Applications and of any and all parent, grandparent, great-grandparent, etc. applications of the Related Applications is incorporated herein by reference to the extent such subject matter is not inconsistent herewith.

SUMMARY

An embodiment provides a method. In one implementation, the method includes but is not limited to transmitting a timing estimate record responsive to a systemic flow of one or more artificial markers. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

An embodiment provides a system. In one implementation, the system includes but is not limited to circuitry for transmitting a timing estimate record responsive to a systemic flow of one or more artificial markers. In addition to the foregoing, other system aspects are described in the claims, drawings, and text forming a part of the present disclosure.

In addition to the foregoing, various other embodiments are set forth and described in the text (e.g., claims and/or detailed description) and/or drawings of the present description.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 1:
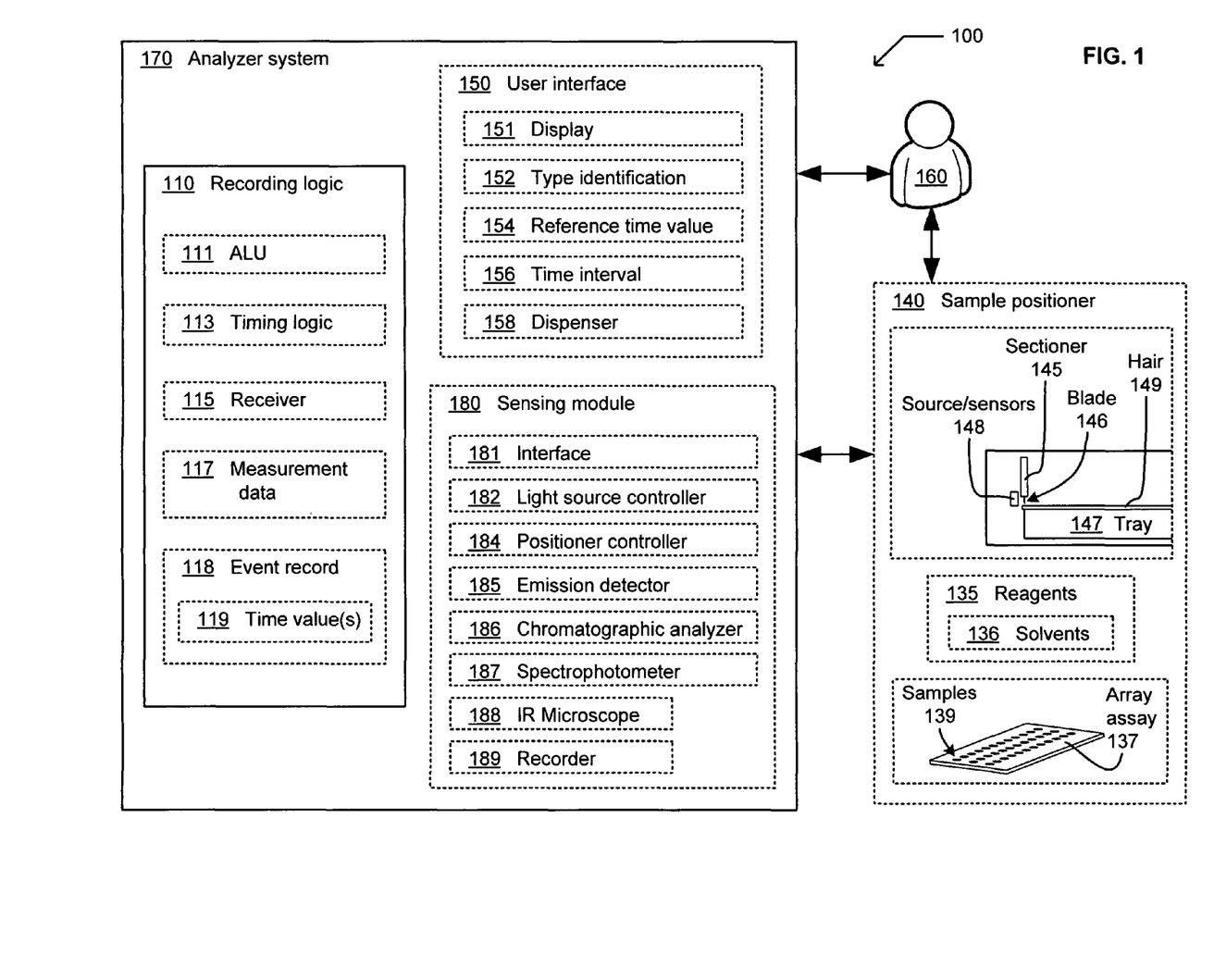
FIG. 1 depicts an exemplary environment in which one or more technologies may be implemented.

Referring now to FIG. 1, there is shown an exemplary environment in which one or more technologies may be implemented. Lab system 100 includes analyzer system 170, and may include sample positioner 140 also, operable by user 160. Analyzer system 170 includes recording logic 110 and may include user interface 150 or sensing module 180 (or both, as explained at the end of this section). Recording logic 110 may include one or more of Arithmetic Logic Unit (ALU)

111, timing logic 113, receiver 115, measurement data 117 from an outgrowth, or event record 118 comprising one or more time values 119.

Any part of measurement data 117 or event record 118 can optionally be analog or digital, scalar- or matrix-valued, and may be buffered, stored, or merely transmitted. Moreover these items may comprise an array of stored values, a message, a control signal, a historical record, or simply an XY-plot or other outcome presented to user 160 via user interface 150 or otherwise used or sent through an external linkage.

In some embodiments, user interface 150 includes one or more of display 151, type identification 152, a reference time value 154, a time interval 156, or a dispenser 158 as exemplified below. These embodiments optionally include sensing module 180 comprising one or more of interface 181, light source controller 182, positioner controller 184, emission detector 185, chromatographic analyzer 186, spectrophotometer 187, infrared (IR) microscope 188, and recorder 189.

Sensing module 180 may include one or more of light source controller 182, positioner controller 184, emission detector 185, chromatographic analyzer 186, spectrophotometer 187, IR microscope 188, or recorder 189. Alternatively or additionally, sensing module 180 can include interface 181 operable to transmit measurement data 117 to receiver 115 or to user interface 150. For example, interface 181 can optionally be operable to request, control or otherwise obtain measurement data 117 from one or more network-accessible, remote, or other external systems such as an analyzer, a spectroscope, a microscope, or a computing system.

Sample positioner 140 optionally includes one or more of solvents 136 or other reagents 135, one or more of array assay 137 containing samples 139, or sectioner 145. As shown in relation to sectioner 145, source/sensors 148 can optionally be included to measure one or more optical responses of a left-most end of hair 149 to a controlled emission from source/sensors 148. As shown, sectioner 145 is controllable to manipulate blade 146 to cut hair 149 very precisely, such as by actuating blade 146 with one or more piezo stacks or MEMS devices (not shown). In this optional example, tray 147 is similarly controllable to translate left (carrying hair 149) or otherwise to push hair 149 left very precisely for further cuttings or measurements, such as by using a stepper motor (not shown). Those skilled in the art can readily implement sectioner 145 with other cutting mechanisms as well, such as a laser or a fine grinding surface. Sectioner 145 can alternatively be implemented as a row or other array of cells each containing a solvent into which an end of hair 149 is dipped (array assay 137, e.g.).

Array assay 137 can contain 36 (forward or reverse) sequential samples of a uniform length of hair, for example, so that each row of three cells receives a sample before proceeding to the next row. In this way each column of 12 cells has a (forward or reverse) sequence of 12 samples temporally and axially interspersed with the other two columns. Such an array can allow for a different testing regimen for each of the three columns even while preserving the sequencing, and even for a sample as small as one or two strands, whether the testing regimen is destructive or not.

It is contemplated that some embodiments of lab system 100 include sample positioner 140, as indicated by its dashed border, and that some do not. For example, samples and/or signals may be received directly in some embodiments of analyzer system 170, in which case lab system 100 can function well even without sample positioner 140 and even without directly accessing any samples.

In some embodiments involving sectioner 145, however, tray 147 can move hair 149 left so far that it extends well beyond source/sensors 148, after which source/sensors 148 can optionally be used for measuring one or more optical properties of a lateral surface of hair 149. In a variant configuration (not shown), a similar configuration of one or more lasers and one or more sensors are positioned "upstream" from sectioner 145 relative to the (leftward) motion of hair 149.

Figure 2:
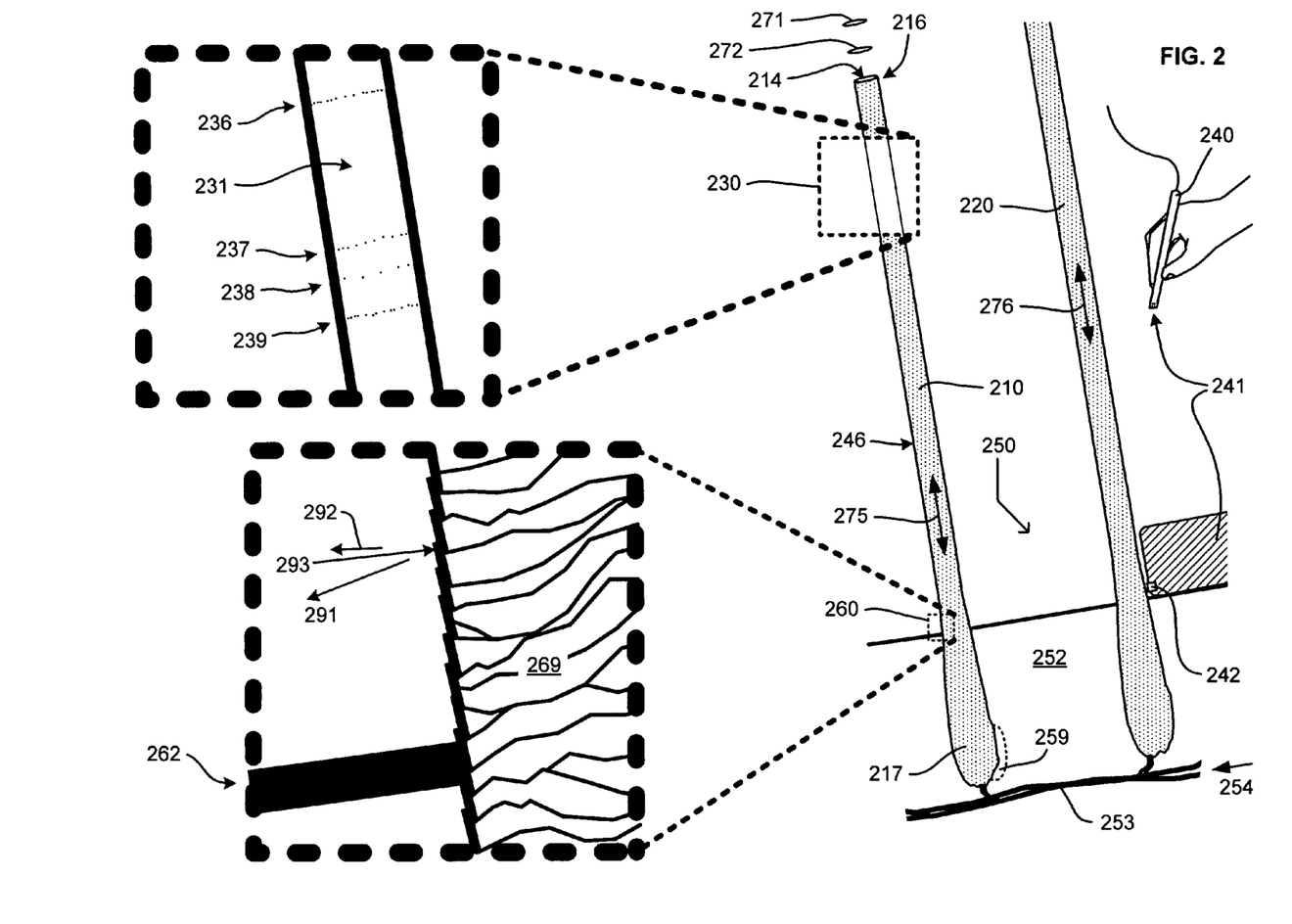
FIG. 2 depicts a highly magnified view of two strands of hair in situ, with a sensor positioner shown for illustration.

Turning now to FIG. 2, there is shown a highly magnified view of two in situ hairs 210, 220 which remain affixed with skin 252 of subject 250 as shown. Hair 210 is substantially aligned along axis 275 within a range of interest longer than 0.5 mm, and hair 220 is substantially aligned along parallel axis 276 within its (shown) range of interest.

Circulatory system (adequately shown as a blood vessel for present purposes) 253 carries blood in a flow 254 that nourishes hair 210 at root 217. Root 217 is the most extreme proximal portion of hair 210, and is also firmly attached to skin tag 259. As shown, portion 271 and portion 272 have been removed from the distal portion of hair 210, which includes surface 214 at end 216. As described below, some embodiments relate to samples of a hair or other outgrowth for which an orientation or growth rate indicator can be useful.

Referring again to hair 210, a more magnified view of longitudinal portion 230 is provided. At least sebum layer 246 has been removed from longitudinal portion 230, revealing lateral surface 231, an exposed portion of the cortex of hair 210. Even without dissolving the cortex of longitudinal portion 230, as described below, it may be possible to detect one or more of an earlier-made marking 236, a naturally-occurring marker 237, a contaminant 238, or a later-made marking 239.

FIG. 2 also provides a more magnified view of lateral portion 260 of hair 210 at skin line 262. That magnified view clearly shows how sebum layer 246 comprises outward-tilting plates 269 that can help establish an orientation of hair 220, for example. The plates are optically assymetrical, so that for example, incident light 293 substantially perpendicular to axis 275 is reflected along ray 291 more than along ray 292. This is one of the inherent assymetries that can be used in some embodiments so that timing logic 113 can determine a signal or sample orientation.

FIG. 2 also shows a hand-held positioner 240 that includes one or more supports 241 (tines, e.g) that bear one or more sensors 242 or guide a sample along relative to the one or more sensors 242 (by sliding an inter-tine groove upward or downward along hair 220, e.g.).

Figure 3:
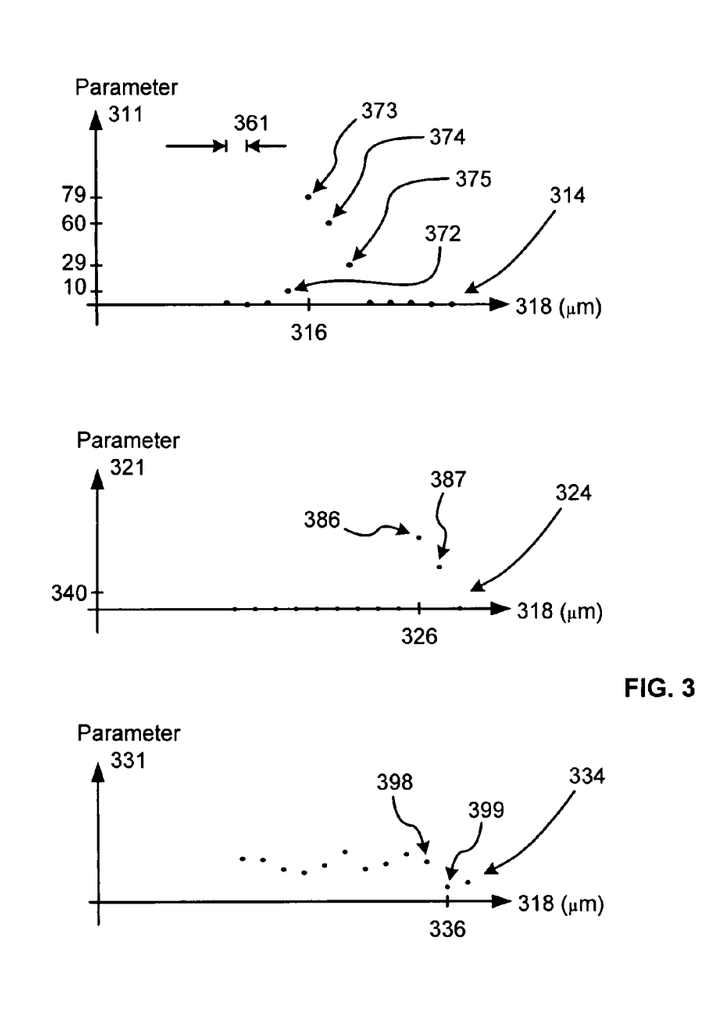
FIG. 3 depicts a plot of several parameters as periodically sampled functions each relating to an outgrowth or outgrowth parameter.

Referring now to FIG. 3, there is shown a plot of parameter 311 as a periodically sampled function 314 of distance 318 such as can obtained by analyzing a first one of the columns of twelve cells of array assay 137 described above. Also shown are plots of parameter 321 and parameter 331 as periodically sampled function 324 and periodically sampled function 334 of distance 318, respectively. Each of these several parameters 311, 321, 331 can be a concentration, a radioactivity, a luminescence, a magnetic response, an electrical resistance or capacitance, a reactivity with an analyte, a bacteria concentration, a temperature, a ratio, or substantially any axially variable, measurable or calculable quantity. In some embodiments in which the outgrowth exhibits a substantially steady, approximately known axial rate, function 314 adequately represents parameter 311 plotted versus time as well.

Function 314 comprises a series of 12 samples having a uniform sampling increment 361 and a detectable peak (at sample 373) at position 316. As shown, measured or calculated values of parameter 311 are 10 (at sample 372), 79 (at sample 373), 60 (at sample 374, and 29 (at sample 375). Function 324 comprises a similar series of 12 samples in which sample 386 and sample 387 exhibit a similar detectable peak (above threshold 340, e.g.) at position 326. Function 334 likewise exhibits a detectable transition at or between sample 398 and sample 399, at position 336.

When a peak, trend, transition, or other marking pattern is detected in one or more signals extracted from a biological recording, those skilled in the art will recognize in light of these teachings that an inference concerning rate or orientation can often be drawn from a timing measurement, computation, or other estimate responsive to the pattern. In some embodiments, for example, parameter 311 indicates a first marker and parameter 321 indicates a second marker. Timing information indicating which of these markers were in a systemic flow later can be used to draw an inference about whether or not distance 318 correlates with successively older outgrowth samples. (Note that parameter 311 or parameter 321 can be a natural marker in some embodiments.) Timing information indicating an offset time between the flows can likewise be used in scaling, for example by estimating an amount of time corresponding with sampling increment 361. Additional examples are provided below.

Figure 4:
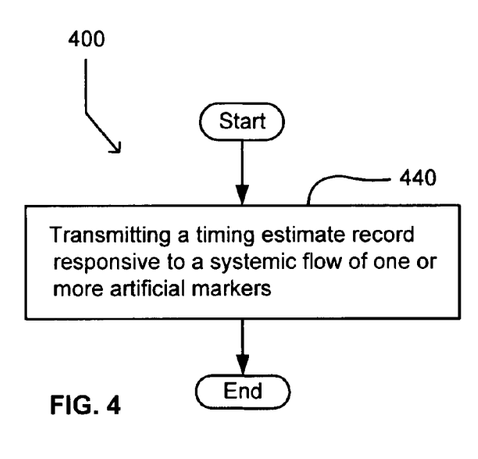
FIG. 4 depicts a high-level logic flow of an operational process.

Referring now to FIG. 4, there is shown a high-level logic flow 400 of an operational process. Operation 440 shows transmitting a timing estimate record responsive to a systemic flow of one or more artificial markers. In some embodiments, the one or more artificial markers include an artificial toxin, a drug, a dye, a set of one or more radioisotopes, a mixture, or other chemical component in a flow sufficient to deposit a detectable quantity in the outgrowth. Alternatively or additionally, the marker(s) can include a heavy metal trace or other natural material selected pro hoc and deposited in a detectable volume for marking the outgrowth via a systemic flow. (The flow can be intentional, spontaneous, artificial, sporadic, or otherwise.) Alternatively or additionally, a timing estimate per se may be the only aspect of the record that is responsive to the flow. Alternatively or additionally, measurement data from separate samples can optionally be combined, for example to align samples or enhance a signal level. See, e.g., U.S. patent application Ser. No. 11/323,832, "Modulating a Biological Recording with Another Biological Recording" filed 30 Dec. 2005 by Hyde et al. and co-owned herewith.

Figure 5:
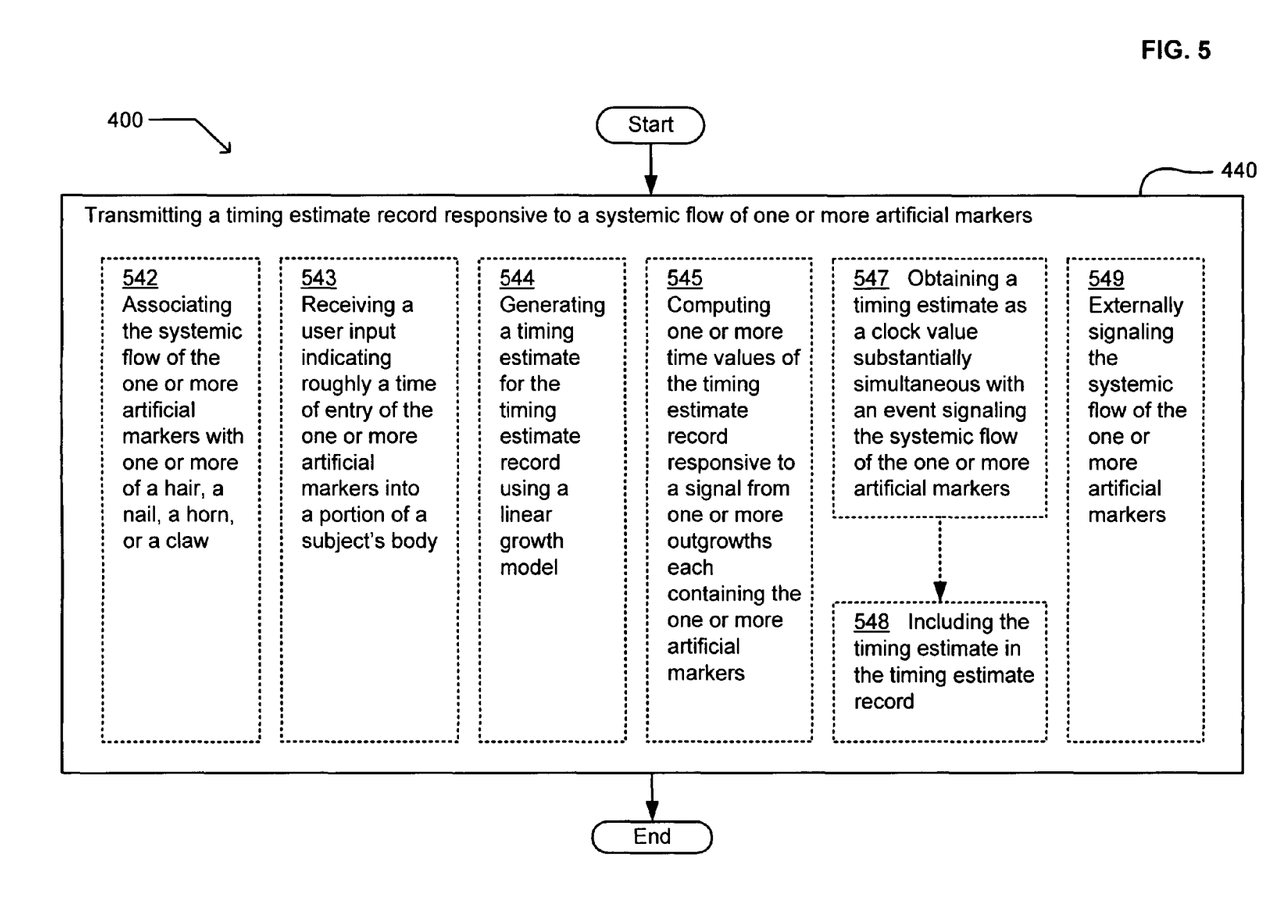
FIG. 5 depicts several variants of the flow of FIG. 4.

Referring now to FIG. 5, there are shown several variants of the flows 400 of FIG. 4. Operation 440—transmitting a timing estimate record responsive to a systemic flow of one or more artificial markers—may include one or more of the following operations: 542, 543, 544, 545, 547, 548, or 549. Operation 542 describes associating the systemic flow of the one or more artificial markers with one or more of a hair, a nail, a horn, or a claw. User interface 150 can perform operation 542, for example by transmitting an indication from user 160 that a hair sample and a toenail sample came from a male elephant that was exposed to a radioactive isotope on the morning of February 11. Associating operation 542 can be performed before or after February 11, in this example, and before or after data is obtained from either sample. In some embodiments, user interface 150 (or user 160) can initiate or otherwise control the systemic isotope flow within the elephant's circulatory system, an acquisition of the isotope-containing samples, or an aspect of taking radioactivity measurements from the samples.

Operation 543 describes receiving a user input indicating roughly a time of entry of the one or more artificial markers into a portion of a subject's body (e.g. user interface 150 receiving a key press in response to showing "swallow the marker capsule" and "hit any key to continue" via display 151). In this example, user interface 150 can set reference time value 154 based on when such a key press occurs, for example by estimating the key press as substantially simultaneous with a marker absorption or with the capsule entering the subject's stomach. In another embodiment, user interface 150 receives time-indicative numerical data from user 160 as a response to asking the user when a marker was injected or inhaled into a subject's circulatory or respiratory system.

Operation 440 can be performed without receiving a user input indicating roughly a time of entry of the one or more artificial markers into a portion of a subject's body as well. Recording logic 110 can assume a time of entry, for example, absent the user input. This time can likewise be established, verified, or negated by sensing module 180 in some embodiments, such as by checking for a signal from a marker-containing "smart capsule." (Such a capsule can include a small transmitter responsive to one or more sensors that can detect a suddenly dark environment and/or a temperature of about 37° C., for example.)

Operation 544 describes generating a timing estimate for the timing estimate record using a linear growth model (e.g. ALU 111 applying a ratio for converting a growth distance to a time interval or other computation, or vice versa, for a given sample or class of outgrowths). For outgrowths having a long and longitudinally steady growth phase, such a growth model can enhance accuracy, especially where applied in interpolating or upon a sample from which the ratio was generated. In one example in which parameter 311 drops from a value of 60 to a value of 29 over a time interval 361, for example, a metabolization rate can be obtained as this (negative) slope. Assuming that a marker concentration increased drastically just after sample 372 was obtained, one skilled in the art can readily estimate a peak concentration time and a peak value of parameter 311 (higher than 79) to the left of position 316.

Operation 545 describes computing one or more time values of the timing estimate record responsive to a signal from one or more outgrowths each containing the one or more artificial markers (e.g., ALU 111 computing an estimate of 11:00 A.M. responsive to detecting a radioactive deposit 5.500 millimeters offset from another marker injected into the elephant exactly ten days later.) In some embodiments, computing operation 545 can be performed by ALU 111 applying a linear projection with a rate dependent on type identification 152 (0.55 mm/day for male elephants, 0.35 mm/day for a human scalp hair, or 0.16 mm/day for human eyelashes, e.g.). ALU 111 optionally applies a nominal growth rate that depends on a subject's gender, the subject's age, a hair type, a race, or another sample-specific or otherwise subject-specific attribute. In other embodiments, recording logic 170 can affirm or enhance the projection's accuracy by extrapolating or interpolating the exposure time (of an isotope exposure, e.g.) based on event record 118 indicating more than one marker being introduced at different times (separated by 48.0 hours, e.g.). In still other embodiments, a non-linear model is used to account for growth phase rate variations based on an a priori model or on several markers introduced at various times of a single season or week.

Operation 547 describes obtaining a timing estimate as a clock value substantially simultaneous with an event signaling the systemic flow of the one or more artificial markers (e.g., recording logic 110 responding to receiving an event-indicative signal transition from user interface 150 or sensing module 180 by latching a then-current value of a digital signal from time reference logic 106). Timing logic 113 can include an oscillator or a receiver of a clock signal external to analyzer system 170, for example. The indicated event can be an input from user 160 or (outgrowth-indicative) measurement data 117 obtained via receiver 115, for example. The clock value can be recorded among time values 119 of event record 118, for example.

Operation 548 describes including the timing estimate in the timing estimate record (e.g. event record 118 can include an estimate of 10:17 A.M. in a set of listed time values 119, optionally storing or transmitting them each with a corresponding one or more event description components. The event description component(s) may comprise items ordinarily found in a medical history or a clinical study, in some embodiments, such as descriptive information specific to a subject, a symptom, a graphic, a marker, a measurement, or a measuring entity. Alternatively or additionally, each event description component may contain any number of measurements corresponding time values.

Operation 549 describes externally signaling the systemic flow of the one or more artificial markers (e.g. display 151 signaling user 160 to begin the systemic flow or signaling recording logic 110 about beginning or detecting a past or planned systemic flow of the one or more markers).

Figure 6:
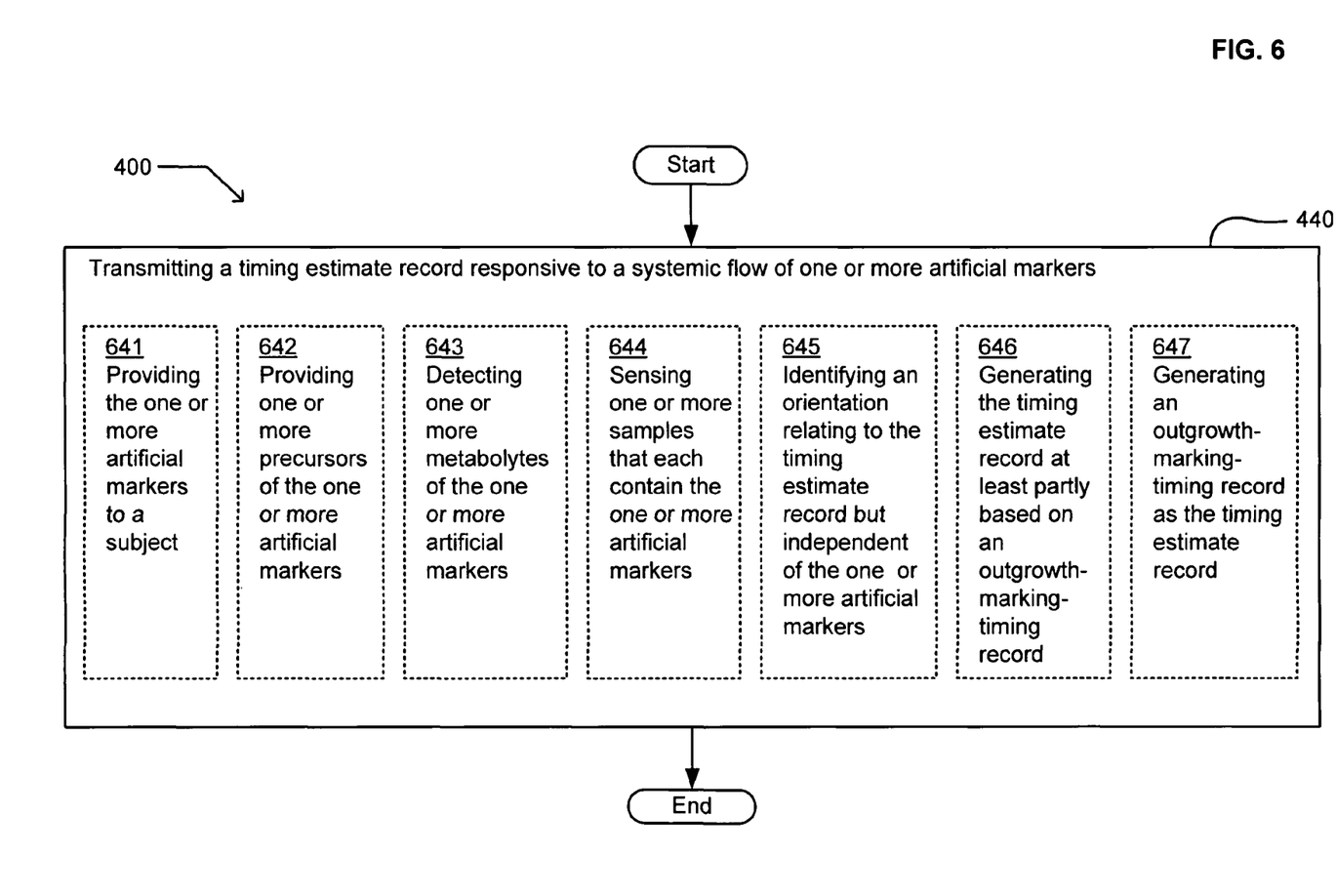
FIG. 6 depicts several variants of the flows of FIG. 4 or FIG. 5.

Referring now to FIG. 6, there are shown several variants of the flows 400 of FIG. 4 or FIG. 5. Operation 440—transmitting a timing estimate record responsive to a systemic flow of one or more artificial markers—may include one or more of the following operations: 641, 642, 643, 644, 645, 646, or 647. Operation 641 describes providing the one or more artificial markers to a subject. Dispenser 158 can provide capsules or some other marker-containing product to user 160 who is the subject, for example. In other embodiments, user 160 can be a nurse or other care provider who injects the artificial marker(s) into a mammal or other subject.

Operation 642 describes providing one or more precursors of the one or more artificial markers. Dispenser 158 can provide one or more substances, for example, that can be combined, metabolized, or otherwise used to generate the one or more artificial markers. Many of the carbohydrate compounds described below in conjunction with operation 644, for example, can be used as the precursor(s) for producing detectable enzymes or lipids in an outgrowth. Alternatively or additionally, a precursor containing a heavy metal (in a first chemical form) can be detected later (whether in the first chemical form or a second chemical form) by a spectrophotometer.

Operation 643 describes detecting one or more metabolites of the one or more artificial markers (e.g. spectrophotometer 187 detecting the "second form" of the above-described heavy-metal-containing substance). An inhaled or ingested substance containing an atypically high (unhealthy) level of mercury, lead, aluminum, iron, nickel, arsenic, or cadmium can, for example, be detected even after a systemic flow or other metabolic processes, chemical or otherwise.

Operation 644 describes sensing one or more samples that each contain the one or more artificial markers (e.g., chromatographic analyzer 186 or spectrophotometer 187 detecting which of the one or more samples 139 of array assay 137 contain a dye or other substance selected for marking), In some embodiments, the substance can be a sugar or sugar derivative such as arabinose, erythrulose, myo-inositol, cis-inositol, mannitol, sorbose, rhamnose, sorbitol, xylose and xylulose. Many such substances are soluble in water and detectable by enzymatic tests. See, e.g., U.S. patent application Ser. No. 10/471,815 ("Method for Sample Identification in a Mammal as Well as a Kit for Performing This Method"), filed 14 Mar. 2002 by Ruprecht Keller, at ¶ 28. Keller also mentions the use of isoprenoids, lipids, saccharides, polyols, polyethylene glycols, derivatives or mixtures of these substances as markers. See id. at ¶ 29. Recognizable carbohydrate compounds such as these can likewise be used in embodiments described herein, whether natural or artificial. See, e.g., Cerling et al., "Stable Isotopes in Elephant Hair Document Migration Patterns and Diet Changes," PNAS, vol. 103, pp 371-37 (10 Jan. 2006). In some embodiments, samples 139 are chopped or ground finely (such as by sectioner 145, e.g.) to disintegrate cells, plates, and other structures in an outgrowth before applying solvents 136 or other reagents 135.

Operation 645 describes detecting one or more metabolites of the one or more artificial markers (e.g. sensor 242 or source/sensors 148 detecting an anatomical or other optical indicator indicating which of a plurality of samples is older without relying on the one or more markers). In some embodiments, recording logic 110 determines whether light 293 orthogonally approaching axis 275 of hair 210 primarily reflects as first ray 291 in a first direction or second ray 292 in a second direction. In some embodiments, user interface 150 is configured to enable user 160 to set or override an orientation identifier if measurement data 117 includes a two-dimensional image indicating a skin tag 259, a bulbous root 217, or a clear image of plates 269.

Operation 646 describes generating the timing estimate record at least partly based on an outgrowth-marking-timing record (e.g. recording logic 110 generating a record containing an estimate of 2:27 P.M. on February 3, a time estimated at least partly based on one or more observations of hair 210). For example, the observations can be captured by one or more sensors 242 sliding substantially from (scalp or other) skin line 262 in a distal direction, or vice versa. In some embodiments, sample positioner 140 comprises a sensor protruding from an end of a pencil-like probe for conveniently scanning along horns or other types of outgrowths.

Operation 647 describes generating an outgrowth-marking-timing record as the timing estimate record (e.g. recording logic 110 indicating in event record 118 that sebum layer 246 contained a cocaine analyte that apparently marked hair 210 during the week of June 11). In some embodiments, a more reliable marking-timing estimate for an outgrowth section (a sebum, e.g.) is generated based on an artificial marking in the same outgrowth section. In some embodiments in which a marker is detected on a surface layer such as a sebum, event record 118 includes an indication that the marker was absent from each reading adjacent the positive reading(s), affirming that the positive reading(s) are likely to have arisen through a systemic flow rather than through a post-emergence application of the marker. Alternatively or additionally, in some embodiments, recording logic 110 can use more than one marking in a common outgrowth section (a cortex, e.g.) so as to reduce an error/offset arising from differing systemic routes into the outgrowth.

Figure 7:
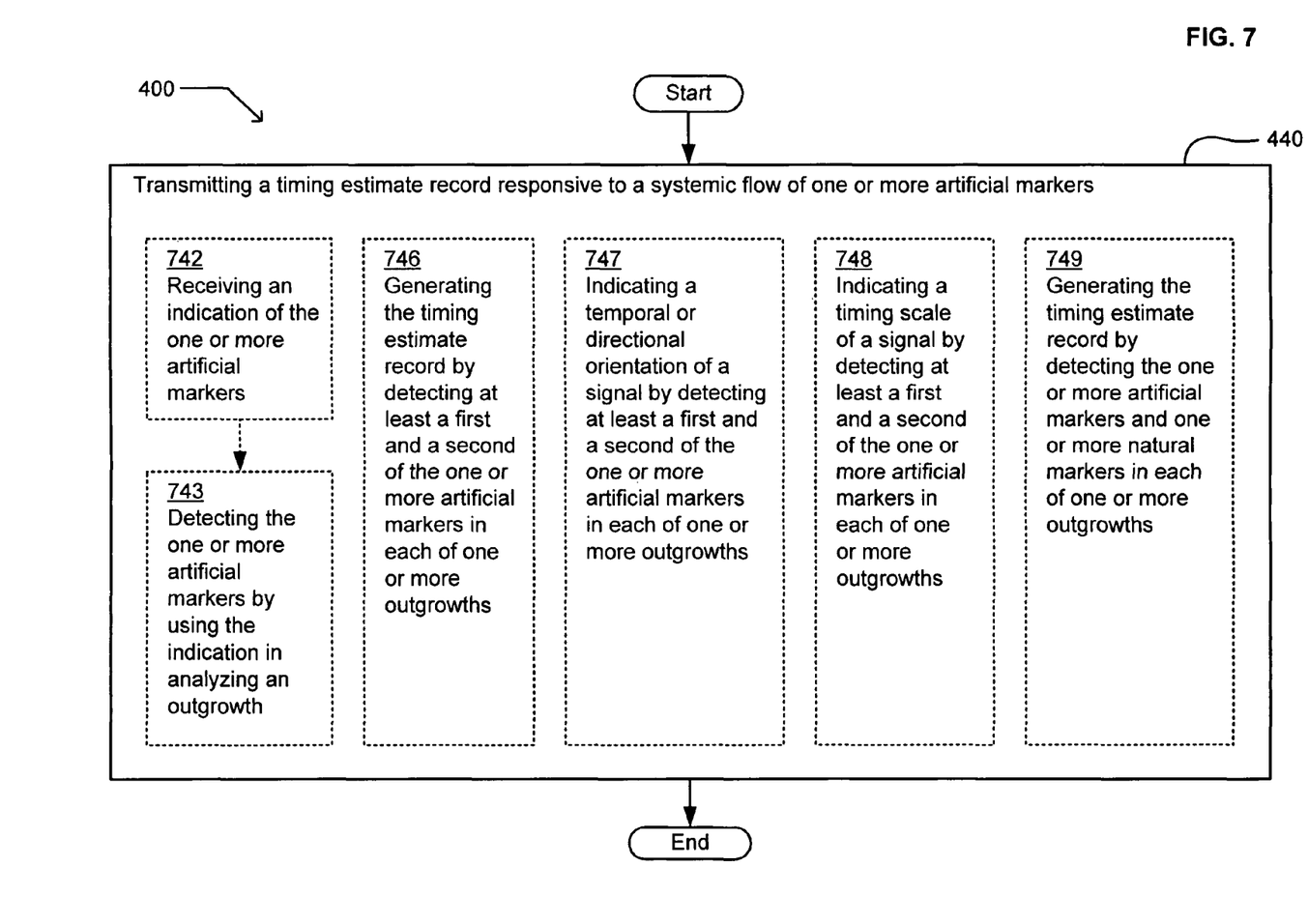
FIG. 7 depicts several other variants of the above-mentioned flows.

Referring now to FIG. 7, there are shown several variants of the flows 400 of FIG. 4, FIG. 5 or FIG. 6. Operation 440-transmitting a timing estimate record responsive to a systemic flow of one or more artificial markers-may include one or more of the following operations: 742, 743, 746, 747, 748, or 749. Operation 742 describes receiving an indication of the one or more artificial markers (e.g. analyzer system 170 receiving an indication via user interface 150 that several doses of heroin were taken during a 5-day period ending exactly 54 days ago). In some embodiments, alternatively or additionally, analyzer system 170 can receive such marker indications via spectrophotometer 187 or emission detector 185 of sensing module 180.

Operation 743 describes detecting the one or more artificial markers by using the indication in analyzing an outgrowth (e.g. analyzer system 170 measuring a detectable quantity of marker portion of the heroin). In some embodiments, those skilled in the art will recognize that such an amount of the marker portion can be found in a metabolized form such as 6-acetylmorphine.

Operation 746 describes generating the timing estimate record by detecting at least a first and a second of the one or more artificial markers in each of one or more outgrowths. Recording logic 110 can detect the first and second of the artificial markers, for example, by recognizing a transition, a trend, a spike, or another readily recognizable pattern in measurement data 117 from an outgrowth via recorder 189. Recording logic can generate the timing estimate record by indicating when (or at what location within a recorded signal) the recognized pattern was found.

Operation 747 describes indicating a temporal or directional orientation of a signal by detecting at least a first and a second of the one or more artificial markers in each of one or more outgrowths (e.g., timing logic 113 identifying "forward" responsive to determining that a later-marked pulse in function 324 is found to the right of an earlier-marked pulse in function 314) In some embodiments, an orientation identifier has a value of "right side up," "distal," "proximal," "opposite," "older," "toward the root," "true," "false," or some other indicator describing which end of a sample or signal is which.

Operation 748 describes indicating a timing scale of a signal by detecting at least a first and a second of the one or more artificial markers in each of one or more outgrowths (e.g., timing logic 113 indicating an amount of time that corresponds with sampling increment 361 at least partly based on an offset between position 316 and position 326).

Operation 749 describes generating the timing estimate record by detecting the one or more artificial markers and one or more natural markers in each of one or more outgrowths (e.g., recording logic 110 generating and storing an estimate of a natural marking time relative to an artificial marking time). Such an estimate may be used to estimate natural marking times in absolute terms, for example. In some embodiments, the accuracy of such estimates is enhanced by providing an accurate record of the artificial marking time(s).

Figure 8:
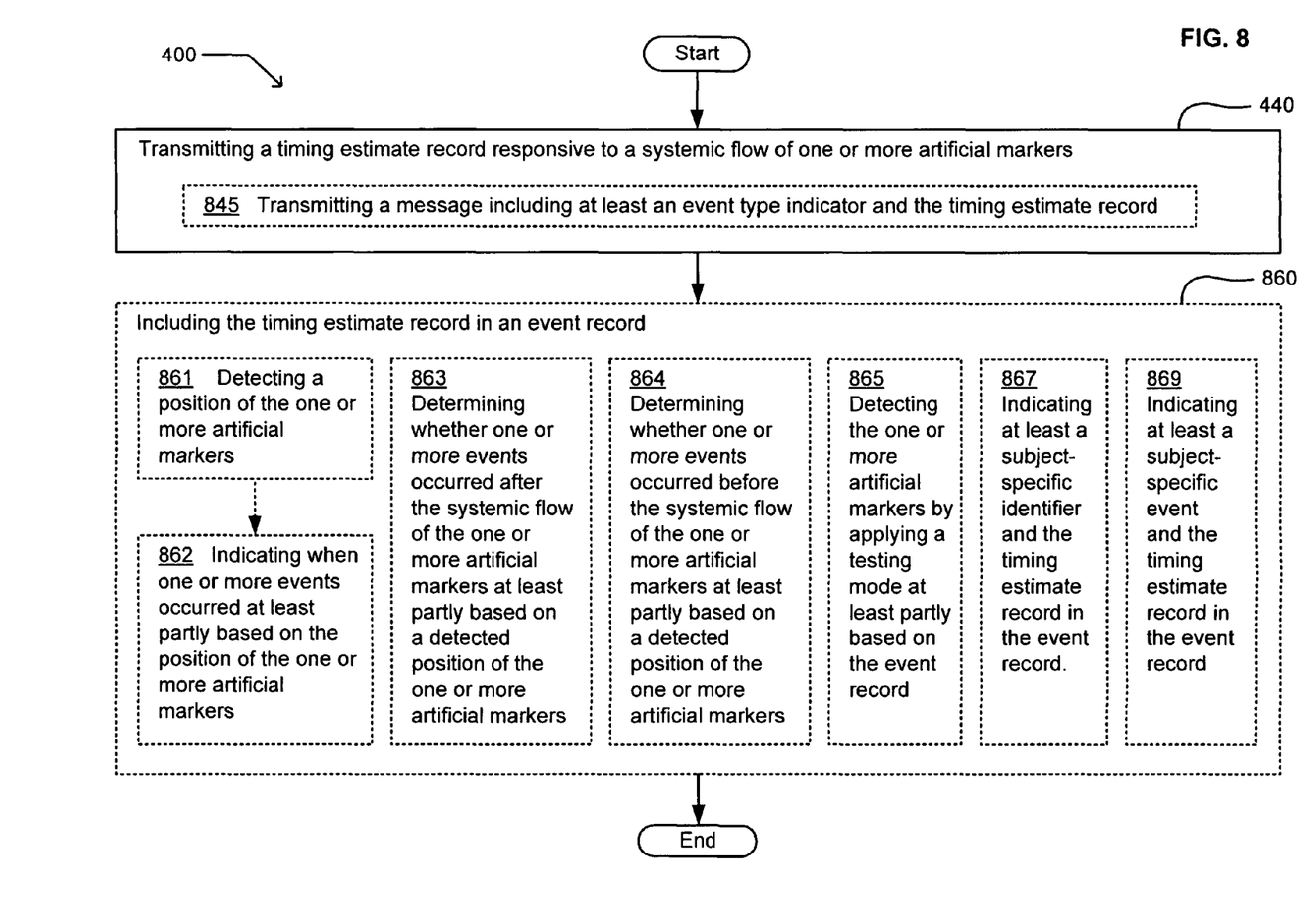
FIG. 8 depicts several further variants of the above-mentioned flows.

Referring now to FIG. 8, there are shown several variants of the flows 400 of FIG. 4, FIG. 5, FIG. 6, or FIG. 7. Operation 440 may include operation 845, for example. Operation 845 describes transmitting a message including at least an event type indicator and the timing estimate record (e.g. user interface 150 displaying or otherwise transmitting a representation of event record 118). The event type indicator may include a marker or marking substance identification, a climate indicator or other environmental status descriptor, a descriptor of a symptom onset or other subject-specific event, or an identifier of an anomaly or other significant change in a signal, for example.

Any of the above-described embodiments of flow 400 may further include operation 860, describing including the timing estimate record in an event record (e.g. event record 118 including more than just one or more time values 119, or recording logic 110 making such an inclusion in cooperation with user interface 150 or sensing module 180). This can include one or more of operation 861, operation 862, operation 863, operation 864, operation 865, operation 867, or operation 869, for example.

Operation 861 describes detecting a position of the one or more artificial markers (e.g. IR microscope 188 generating an image in which the one or more artificial markers are automatically or manually apparent). Sensing module 180 can generate such images using light source controller 182, store them in recorder 189, and later transmit them to receiver 115 in some embodiments, for example. In other embodiments, receiver 115 obtains a signal from remote equipment via interface 181.

Operation 862 describes indicating when one or more events occurred at least partly based on the position of the one or more artificial markers (recording logic 110 applying one or more criteria to detect a signal pulse or trend in function 334, e.g., and indicating that a significant drop in parameter 331 occurred at 4:22 P.M., which corresponds to position 336)

Operation 863 describes determining whether one or more events occurred after the systemic flow of the one or more artificial markers at least partly based on a detected position of the one or more artificial markers (e.g. recording logic 110 indicating whether a transition in function 334 represents a later event than that of a marker-density peak at position 316, at least partly based on a pattern in function 324). In some embodiments, the detected position can reflect a pulse skew such as that of function 314, for example, reflecting an artificial marker distribution that transitions more sharply on the left side than on the right. Such a pattern can indicate a sudden influx followed by a more gradual metabolization of the marker, for example. In other embodiments in which the artificial marker(s) were released at irregular intervals, in some embodiments, a resulting asymmetrical pattern can be used to generate orientation and other timing information with decoding technology by which barcode and other symbol-reading signals are interpreted. See, e.g., U.S. Pat. No. 5,296,690 ("System for Locating and Determining the Orientation of Bar Codes in a Two-Dimensional Image") issued 22 Mar. 1994 to Chandler et al.

Operation 864 describes determining whether one or more events occurred before the systemic flow of the one or more artificial markers at least partly based on a detected position of the one or more artificial markers (e.g. recording logic 110 indicating whether a transition in function 324 represents an earlier event than that of a pattern at position 316 based on a pattern in each of function 314, function 324, and function 334).

Operation 865 describes detecting the one or more artificial markers by applying a testing mode at least partly based on the event record (e.g. sensing module 180 deciding which one or more of interface 181, light source controller 182, emission detector 185, chromatographic analyzer 186, spectrophotometer 187, or IR microscope 188 to use, responsive to a portion of event record 118). Event record 118 can in turn depend, in some embodiments, on prior input from user interface 150 or sensing module 180.

Operation 867 describes indicating at least a subject-specific identifier and the timing estimate record in the event record (e.g. event record 118 including one or more time values 119 as well as a name or number describing a subject or a sample of a subject to which the one or more time values 119 relates). The subject-specific identifier can optionally identify the subject uniquely, in some embodiments, such as by including a social security number or a complete DNA-based identifier. In other embodiments, the subject-specific identifier is only sufficient to identify the subject uniquely within a given class, such as by including only one of an employer name or an employee number.

Operation 869 describes indicating at least a subject-specific event and the timing estimate record in the event record. Event record 118 can include an indication that patient Alan Smith took a marker-containing medication every day in October, for example.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

While particular aspects of the present subject matter described herein have been shown and described, it will be apparent to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that any disjunctive word and/or phrase presenting two or more alternative terms, whether in the description, claims, or drawings, should be understood to contemplate the possibilities of including one of the terms, either of the terms, or both terms.

For example, the phrase "A or B" will be understood to include the possibilities of "A" or "B" or "A and B." Moreover, "can" and "optionally" and other permissive terms are used herein for describing optional features of various embodiments. These terms likewise describe selectable or configurable features generally, unless the context dictates otherwise.

The herein described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable and/or physically interacting components and/or wirelessly.

What is claimed is:

1. A method for generating a timing estimate record associated with systemic flow of at least one artificial marker comprising:
   receiving at least one indication of at least one artificial marker by moving at least one sensor along a length of at least one outgrowth while the at least one outgrowth remains in situ;
   determining, using the at least one sensor, at least one distance of the at least one artificial marker from a root of the at least one outgrowth; and
   generating a timing estimate record associated with systemic flow of the at least one artificial marker using the at least one distance.

2. The method of claim 1, in which generating the timing estimate record associated with systemic flow of the at least one artificial marker further comprises:
   determining, via user input, roughly a time of entry of the at least one artificial marker into a portion of a subject's body.

3. The method of claim 1, in which generating the timing estimate record associated with systemic flow of the at least one artificial marker further comprises:
   obtaining a timing estimate as a clock value substantially simultaneous with an event signaling the systemic flow of the at least one artificial marker; and
   including the timing estimate in the timing estimate record.

4. The method of claim 1, in which generating the timing estimate record associated with systemic flow of artificial marker further comprises:
   externally signaling the systemic flow of the at least one artificial marker.

5. The method of claim 1, in which generating the timing estimate record associated with systemic flow of the at least one artificial marker further comprises:
   generating the timing estimate record at least partly based on an outgrowth-marking-timing record.

6. The method of claim 1, further comprising:
   determining at least one relative position of the at least one artificial marker to one or more natural markers in the at least one outgrowth.

7. The method of claim 1, in which generating the timing estimate record associated with systemic flow of the at least one artificial marker further comprises:
   generating at least an event type indicator.

8. The method of claim 1, wherein generating the timing estimate record associated with systemic flow of the at least one artificial marker further comprises:
   receiving, from a capsule containing one or more artificial markers, and upon the capsule reaching a specified temperature, at least one signal usable to generate the timing estimate record.

9. The method of claim 1, further comprising:
   determining a distance, along the at least one outgrowth, of at least one different marker from the at least one artificial marker; and
   determining at least one event time value of one or more events affecting the outgrowth that are different from the systemic flow of the at least one artificial marker in response to the at least one distance of the at least one different marker from the at least one artificial marker.

10. The method of claim 1, further comprising:
    determining a relative position, along the at least one outgrowth, of the at least one artificial marker to at least one different marker; and
    determining an orientation based upon the at least one relative position.

* * * * *